(12) United States Patent
Chae et al.

(10) Patent No.: US 11,974,867 B2
(45) Date of Patent: May 7, 2024

(54) ADJUSTABLE COUCH AND MEDICAL COUCH SYSTEM COMPRISING SAME

(71) Applicant: Samsung Life Public Welfare Foundation, Seoul (KR)

(72) Inventors: Moon Ki Chae, Seoul (KR); Dong Yeol Kwon, Gyeonggi do (KR); Sung Hoon Joo, Seoul (KR)

(73) Assignee: Samsung Life Public Welfare Foundation, Seoul (KR)

( * ) Notice: Subject to any disclaimer, the term of this patent is extended or adjusted under 35 U.S.C. 154(b) by 538 days.

(21) Appl. No.: 17/288,159

(22) PCT Filed: Sep. 25, 2019

(86) PCT No.: PCT/KR2019/012441
§ 371 (c)(1),
(2) Date: Apr. 23, 2021

(87) PCT Pub. No.: WO2020/085659
PCT Pub. Date: Apr. 30, 2020

(65) Prior Publication Data
US 2021/0378607 A1    Dec. 9, 2021

(30) Foreign Application Priority Data
Oct. 25, 2018   (KR) .................. 10-2018-0128318

(51) Int. Cl.
*A61B 6/04*    (2006.01)
(52) U.S. Cl.
CPC .................. *A61B 6/0407* (2013.01)

(58) Field of Classification Search
CPC ......... A61B 6/04; A61B 6/0407; A61B 34/30; A61G 13/00; A61G 13/02; A61G 13/04; A61N 5/10; G05B 15/00
See application file for complete search history.

(56) References Cited

U.S. PATENT DOCUMENTS

| 5,013,018 A | 5/1991 | Sicek et al. |
| 6,094,760 A * | 8/2000 | Nonaka ................ A61N 5/10 5/601 |
| 8,674,326 B2 * | 3/2014 | Iwata .................. A61B 6/032 5/601 |

(Continued)

FOREIGN PATENT DOCUMENTS

| JP | 3577221 B2 | 10/2004 |
| JP | 5984261 B2 | 9/2016 |

OTHER PUBLICATIONS

International Search Report (including English translation of ISR) and Written Opinion prepared by Korean Intellectual Property Office, acting as the International Searching Authority, for international application PCT/KR2019/012441 mailed Dec. 27, 2019.

*Primary Examiner* — Justin C Mikowski
*Assistant Examiner* — George Sun
(74) *Attorney, Agent, or Firm* — McCarter & English, LLP (57) ABSTRACT

An embodiment of the present disclosure provides an adjustable couch that can be mounted on a medical couch, the adjustable couch comprising: a first couch provided with a fixing means to be fixed to the medical couch; and a second couch disposed on the first couch and provided with a rotating-coupling means to be coupled rotatably about a first axis perpendicular to an upper surface of the first couch.

12 Claims, 6 Drawing Sheets

(56) References Cited

U.S. PATENT DOCUMENTS

| | | | |
|---|---|---|---|
| 9,440,094 B2 | 9/2016 | Filiberti | |
| 2004/0143905 A1* | 7/2004 | Pastyr | A61B 6/0407 5/81.1 R |
| 2005/0234327 A1* | 10/2005 | Saracen | A61B 6/548 600/407 |
| 2006/0133580 A1* | 6/2006 | Vezina | A61G 1/0287 378/177 |
| 2010/0319128 A1* | 12/2010 | Kuro | A61B 6/0487 5/601 |
| 2011/0107515 A1* | 5/2011 | Brunker | A61N 5/10 5/601 |
| 2012/0138065 A1* | 6/2012 | Campagna | A61B 6/04 128/845 |
| 2014/0275697 A1* | 9/2014 | Filiberti | A61N 5/107 128/845 |
| 2014/0345054 A1* | 11/2014 | Kodaira | A61B 6/547 5/600 |
| 2016/0287458 A1* | 10/2016 | Skursky | A61G 13/125 |
| 2017/0172673 A1* | 6/2017 | Yu | A61G 13/102 |
| 2018/0321336 A1* | 11/2018 | Carlsson | A61B 5/055 |

* cited by examiner

ADJUSTABLE COUCH AND MEDICAL
COUCH SYSTEM COMPRISING SAME

CROSS-REFERENCE TO RELATED APPLICATIONS

This application is the National Stage entry under 35 U.S.C. § 371 of International Application Number PCT/KR2019/012441 filed on Sep. 25, 2019, published on Apr. 30, 2020 under publication number WO 2020/085659 A1, which claims the benefit of priority under 35 U.S.C. § 119 of Korean patent application number 10-2018-0128318 filed Oct. 25, 2018.

TECHNICAL FIELD

Embodiments of the present disclosure relates to an adjustable couch and a medical couch system comprising same.

BACKGROUND ART

Radiation treatment is a method of clinical medicine for treating patients by using radiation having very short wavelengths and high energy, and is one of the three major cancer treatment methods along with surgery and chemotherapy. This usually treats malignant tumors referred to as cancers but also treats benign tumors and some benign diseases. The radiation treatment may be classified into external radiation treatment and brachytherapy according to the position of an irradiator.

The external radiation treatment is a treatment method of irradiating with radiation by using various pieces of equipment outside the body, and may be classified into photon beam treatment, electron beam treatment, and particle beam treatment such as neutron treatment and proton treatment according to the type of radiation used. Meanwhile, the brachytherapy is a method of irradiating a limited region with radiation by positioning a radiation generator or radioactive isotopes in or on the body, and may be classified into intracavitary treatment, intraluminal treatment, interstitial treatment, contact treatment, or the like according to the insertion space or method thereof.

Meanwhile, when the radiation treatment is performed, successful radiation treatment is possible only by intensively irradiating a target site with high dose while minimizing the damage to normal organs due to the radiation. However, a conventional radiation treatment apparatus, especially, a tomotherapy apparatus is provided such that a roll direction of a couch is adjustable, and thus, when the couch is tilted in the roll direction, it may be adjusted, but there is a problem that adjustment in a yaw direction is impossible.

The background art described above is technical information possessed to derive the present disclosure or learned in the course of deriving the present disclosure by the inventor, and cannot necessarily be said to be a known art published to the general public before filing of the present disclosure.

DESCRIPTION OF EMBODIMENTS

Technical Problem

Embodiments of the present disclosure provides an adjustable couch, which is adjustable in a yaw direction, and a medical couch system comprising same.

Solution to Problem

An embodiment of the present disclosure provides an adjustable couch that can be mounted on a medical couch, the adjustable couch comprising: a first couch provided with a fixing means to be fixed to the medical couch; and a second couch disposed on the first couch and provided with a rotating-coupling means to be coupled rotatably about a first axis perpendicular to an upper surface of the first couch.

Advantageous Effects of Disclosure

An adjustable couch according to embodiments of the present disclosure is provided detachably on a medical couch, and thus it is not necessary to replace the entire medical couch used in radiation treatment for adjustment in a yaw direction, thereby making it possible to achieve an effect of reducing costs. Also, the adjustable couch is adjusted in the yaw direction, and then the radiation treatment may be performed. Through this, the medical couch system may not only decrease the number of retakes as much as possible to reduce the total treatment time, but also accordingly reduce the risk of developing secondary cancer, increase the patient reproducibility, and reduce pains.

BEST MODE

An embodiment of the present disclosure provides an adjustable couch mountable on a medical couch, the adjustable couch comprising: a first couch provided with a fixing means to be fixed to the medical couch; and a second couch disposed on the first couch and provided with a rotating-coupling means to be coupled rotatably about a first axis perpendicular to an upper surface of the first couch.

In an embodiment of the present disclosure, the fixing means may be disposed on a lower surface of the first couch on the opposite side from the upper surface, and may be constituted by one or more first protrusions corresponding to one or more first grooves provided in the medical couch.

In an embodiment of the present disclosure, when the first grooves are constituted by a plurality grooves, the number of the first protrusions may be less than the number of the first grooves.

In an embodiment of the present disclosure, the rotating-coupling means may be constituted by a second protrusion which is disposed on a lower surface of the second couch which is in contact with the upper surface of the first couch.

In an embodiment of the present disclosure, a second groove may be formed, at a position corresponding to the second protrusion, in the upper surface of the first couch.

In an embodiment of the present disclosure, the rotating-coupling means may be constituted by the same material as the second couch.

In an embodiment of the present disclosure, the rotating-coupling means may be disposed on the first axis, but may be disposed at a position different from a center of the first couch.

In an embodiment of the present disclosure, the second couch may be further provided with a rotation angle checking portion through which a rotation angle about the first axis is checked.

An embodiment of the present disclosure provides a medical couch system comprising: a medical couch provided with one or more first grooves; a support for supporting the medical couch; and an adjustable couch which is detachably mounted on the medical couch, and comprises a first couch provided with a fixing means to be fixed to the medical couch and a second couch disposed on the first couch and provided with a rotating-coupling means to be coupled rotatably about a first axis perpendicular to an upper surface of the first couch.

In an embodiment of the present disclosure, the fixing means may be disposed on a lower surface of the first couch on the opposite side from the upper surface, and may be constituted by one or more first protrusions corresponding to one or more first grooves provided in the medical couch.

In an embodiment of the present disclosure, the first grooves may be constituted by a plurality of grooves and disposed at both edges on an upper surface of the medical couch along a first direction in which a length of the medical couch extends, wherein the number of the first protrusions is less than the number of the first grooves.

In an embodiment of the present disclosure, the rotating-coupling means may be constituted by a second protrusion which is disposed on a lower surface of the second couch which is in contact with the upper surface of the first couch.

In an embodiment of the present disclosure, a second groove may be formed, at a position corresponding to the second protrusion, in the upper surface of the first couch.

In an embodiment of the present disclosure, the rotating-coupling means may be constituted by the same material as the second couch.

In an embodiment of the present disclosure, the rotating-coupling means may be disposed on the first axis, but may be disposed at a position different from a center of the first couch.

In an embodiment of the present disclosure, the second couch may be further provided with a rotation angle checking portion through which a rotation angle about the first axis is checked.

Aspects, features, and advantages other than those described above will become apparent from the accompanying drawings, the claims, and the detailed description.

MODE OF DISCLOSURE

Since the present disclosure may be diversely modified and have various embodiments, specific embodiments are exemplified in the drawings and described in detail in the detailed description. Effects and features of the present disclosure, and implementation methods thereof will be clarified through following embodiments described in detail with reference to the drawings. However, the present disclosure is not limited to the embodiments set forth herein, but may be embodied in various forms.

Hereinafter, embodiments of the present disclosure are described in detail with reference to the accompanying drawings, and when describing with reference to the drawings, the identical or corresponding components are given with the same reference numerals, and their duplicated descriptions will be omitted.

In the following embodiments, terms "first" and "second" are used to distinguish one component from another component, but these components should not be limited by these terms.

In the following embodiments, the singular forms include the plural forms as well, unless the context clearly indicates otherwise.

In the following embodiments, the terms "includes" or "including" when used in this specification are to specify the presence of stated features or components, but do not preclude the addition of one or more other features or components.

In the following embodiments, when a portion such as a layer, a region, or a component is referred to as being "above" or "on" another portion, it can be directly on another portion, or another layer, region, or component may also be present therebetween.

In the drawings, the dimensions of elements may be exaggerated or downscaled for convenience of description. For example, since the size and thickness of each component shown in the drawings are arbitrarily shown for convenience of description, and the present disclosure is not necessarily limited thereto.

When a certain embodiment may be implemented differently, a specific process order may be performed differently from the described order. For example, two consecutively described processes may be performed substantially at the same time or performed in an order opposite to the described order.

In the following embodiments, when a layer, a region, a component, and the like are referred to as being connected to each other, not only are the layer, the region, and the component directly connected to each other, but the layer, the region, and the component are indirectly connected to each other with another layer, region, and component interposed therebetween. For example, when a layer, a region, a component, and the like are referred to as being electrically connected to each other in the specification, not only are the layer, the region, and the component directly electrically connected to each other, but the layer, the region, and the component are indirectly electrically connected to each other with another layer, region, and component interposed therebetween.

Figure 1:
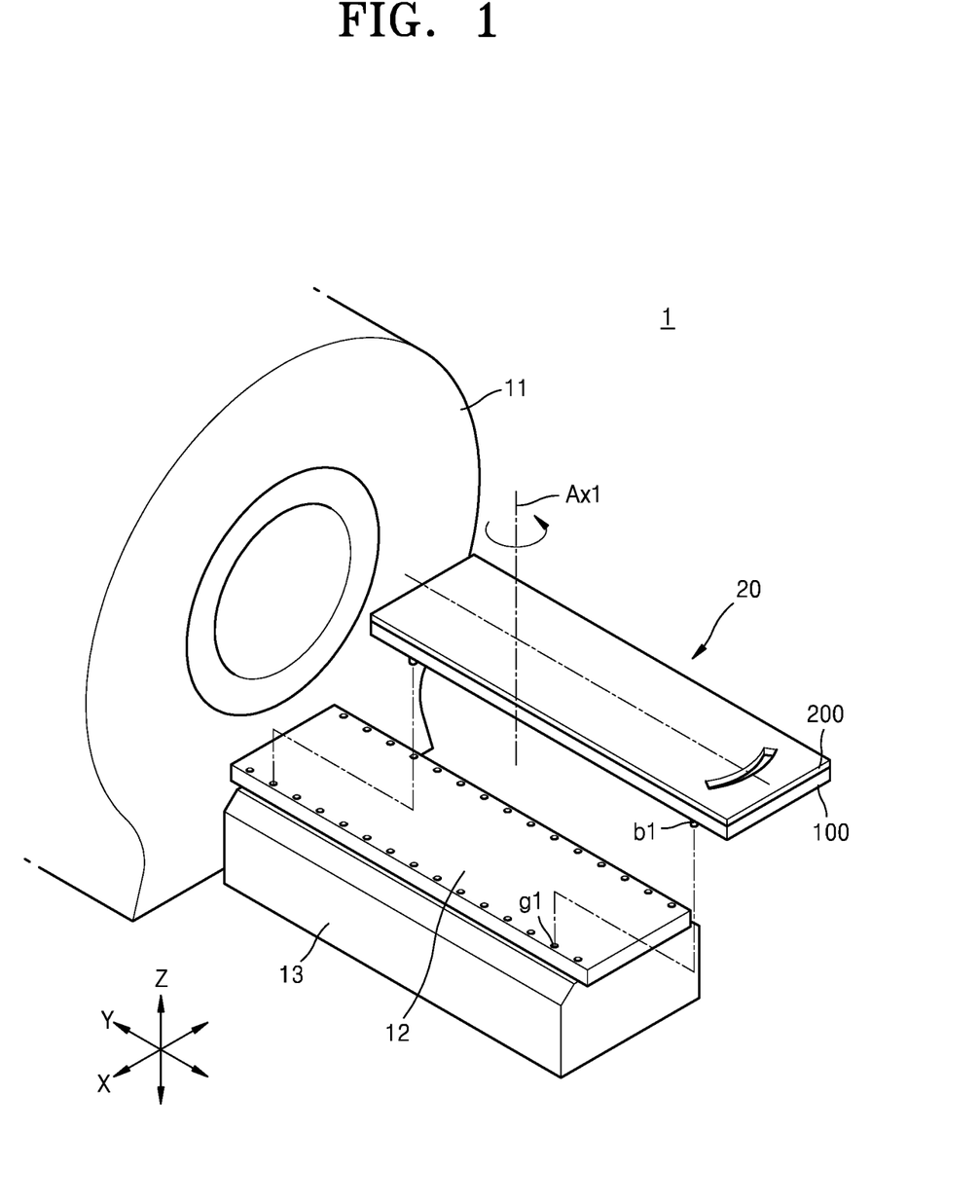
FIG. 1 is a view schematically illustrating a medical couch system according to an embodiment of the present disclosure.

FIG. 1 is a view schematically illustrating a medical couch system 1 according to an embodiment of the present disclosure.

Referring to FIG. 1, the medical couch system 1 may be provided with a radiation treatment device 11, a medical couch 12, a support 13, and an adjustable couch 20.

The radiation treatment device 11 may be provided with a gantry and a radiation irradiation unit. The gantry is provided in the form of arc and may rotate about a patient. For example, the gantry may be provided in the cylindrical structure having a bore, and this may comprehensively mean a partially cylindrical case. Particularly, a bore may be formed in the gantry from one side of the gantry to the other side of the gantry, and the patient may be guided into the bore.

The radiation irradiation unit is disposed on one side of the bore and may irradiate the patient guided into the bore with radiation beams. For example, the radiation irradiation unit may irradiate the patient with the radiation beams to measure tissue displacement or obtain CT images prior to the radiation treatment, and may irradiate the patient with the radiation beams for the radiation treatment during the radiation treatment. Particularly, the radiation irradiation unit may include a linear accelerator and a multi-leaf collimator (MLC). Also, the MLC may investigate the intensity or pattern of radiation beams discharged from the linear accelerator. For example, when a large or small amount of radiation beams is required to treat treatment target tissues of the patient, the intensity of radiation beams may be adjusted in the MLC, and when the treatment target tissues of the patient are displaced, the pattern of the radiation beams are adjusted in the MLC so that the treatment target tissues of the patient are irradiated with the radiation beams.

The medical couch 12 may be provided as a table on which a patient may lie, and one or more first grooves g1 may be provided in an upper surface thereof. The medical couch 12 may be supported by the support 13 which is disposed on a lower surface of the medical couch 12. The medical couch 12 may move into the bore of the radiation treatment device 11. The medical couch 12 may be provided with an adjustable means which is adjustable with respect to a pitch direction (x-axis rotation) and a roll direction (y-axis rotation).

The medical couch system 1 having the above-described configuration is not provided with an adjustable means with respect to a yaw direction inside the medical couch 12, and the adjustment with respect to the yaw direction is possible through the adjustable couch 20 detachably mounted on the medical couch 12.

Figure 2:
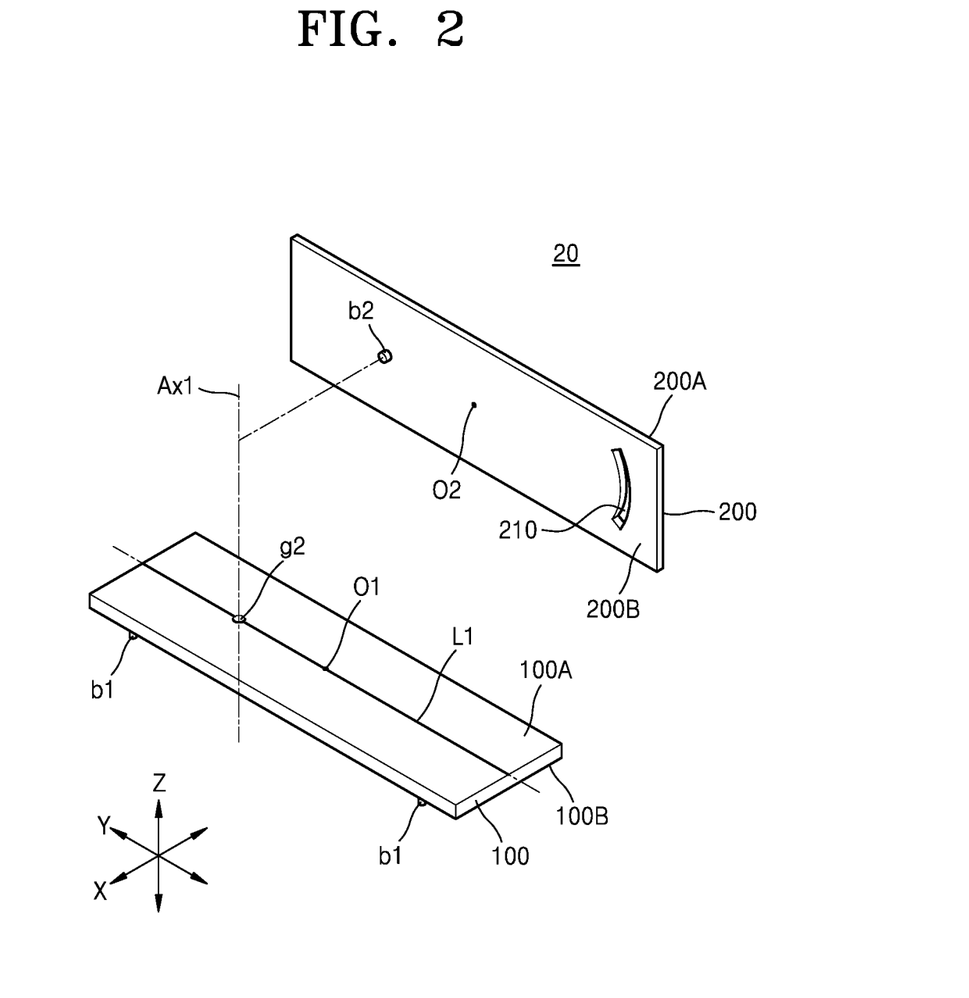
FIG. 2 is a view for describing an adjustable couch of FIG. 1.
Figure 3A:
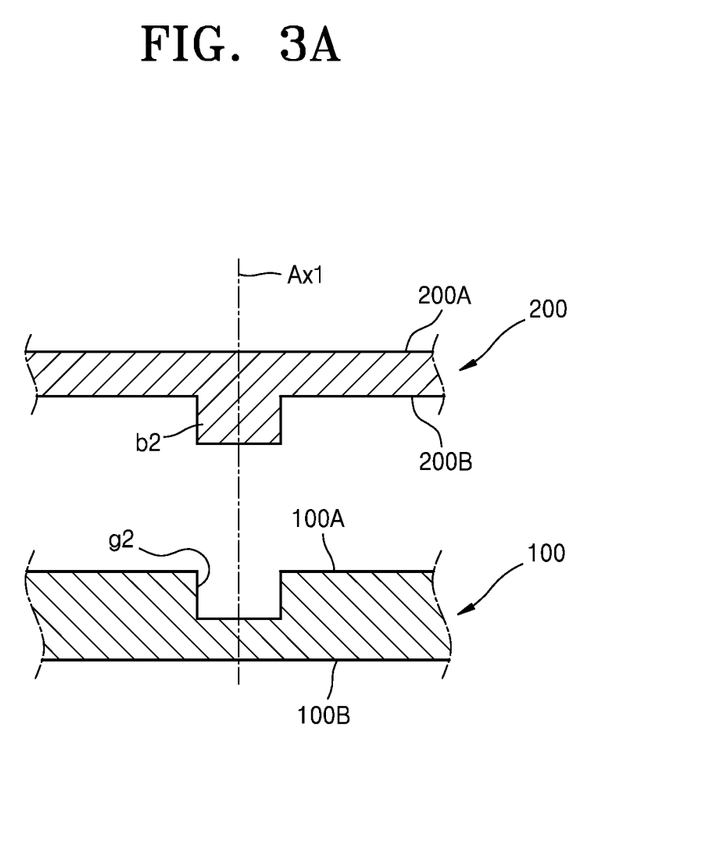
FIGS. 3a and 3b are enlarged cross-sectional views in which some portions are extracted to describe a rotating-coupling means of FIG. 2.
Figure 3B:
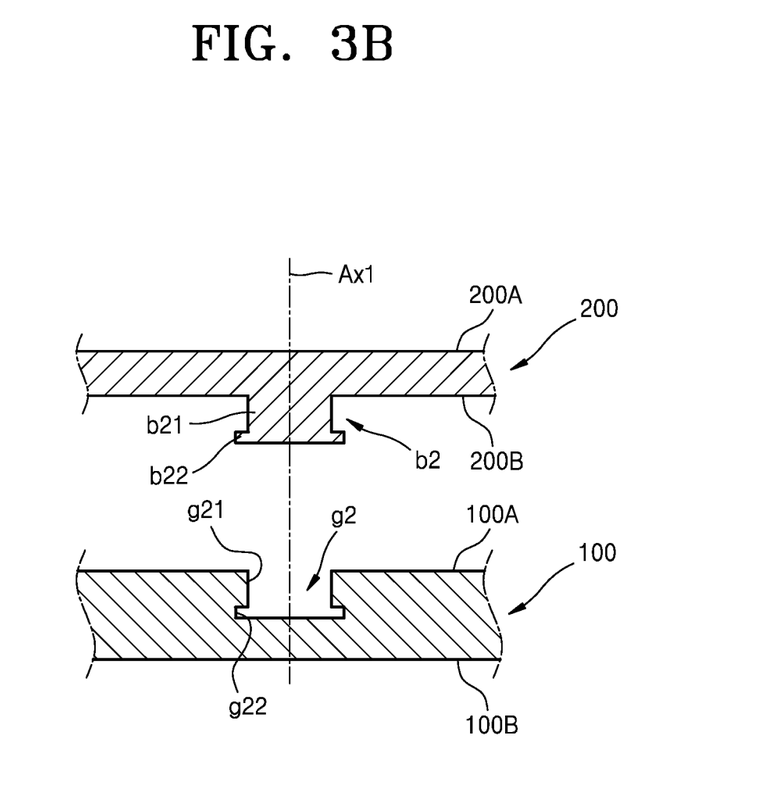

FIG. 2 is a view for describing the adjustable couch 20 of FIG. 1, and FIGS. 3a and 3b are enlarged cross-sectional views in which some portions are extracted to describe a rotating-coupling means b2 of FIG. 2.

Referring to FIG. 2, the adjustable couch 20 may be provided with a first couch 100 and a second couch 200 and may be detachably provided on the medical couch 12.

Particularly, the first couch 100 may be provided with a fixing means b1 to be fixed to the medical couch 12. The fixing means b1 may be disposed on a lower surface 100B of the first couch 100 on the opposite side from an upper surface 100A, and may be constituted by one or more first protrusions corresponding to one or more first grooves g1 provided in the medical couch 12.

As illustrated in FIG. 1, the medical couch 12 may be provided with the plurality of first grooves g1 on an upper surface thereof. The plurality of first grooves g1 may be arranged in a line along both edges on the upper surface of the medical couch 12 in a longitudinal direction (y-axis direction) of the medical couch 12. The fixing means b1 is provided as the first protrusions disposed at positions corresponding to the first grooves g1, and as the first protrusions are inserted into the first grooves g1, the adjustable couch 20 including the first couch 100 may be mounted to the medical couch 12.

Here, the number of first protrusions may be less than the number of first grooves g1. For example, the first grooves g1 may be disposed in a line on both the edges of the medical couch 12 along the longitudinal direction, and the first protrusions may be constituted by a pair of protrusions which are disposed symmetrically with respect to the longitudinal direction (the y-axis direction) to be able to correspond to any one pair of first grooves g1 among the first grooves g1. Through this, the fixing means b1 may be stably fixed to an upper end of the medical couch 12. However, the technical idea of the present disclosure is not limited thereto, and in another embodiment, any means such as a clamp capable of fixing the adjustable couch 20 on the medical couch 12 may be applied.

Meanwhile, the first couch 100 may be provided with a second groove g2 in the upper surface 100A thereof.

The second couch 200 is disposed on the first couch 100, and may be provided with a rotating-coupling means b2 to be coupled rotatably about a first axis Ax1 perpendicular to the upper surface 100A of the first couch 100. The rotating-coupling means b2 may be constituted by a second protrusion which is disposed on a lower surface 200B of the second couch 200 which is in contact with the upper surface 100A of the first couch 100. The rotating-coupling means b2 constituted by the second protrusion is inserted into the second groove g2 of the first couch 100 and may couple the first couch 100 and the second couch 200.

Referring to FIGS. 2 and 3a, the second protrusion b2, which is the rotating-coupling means, is formed in a cylindrical shape, and may couple the first couch 100 and the second couch 200 and also allow the second couch 200 to be rotatable with respect to the first couch 100 fixed to the medical couch 12. Particularly, the rotating-coupling means b2 may rotate the second couch 200 about the first axis Ax1 perpendicular to a plane direction (the x-y direction) of the medical couch 12. Here, the first axis Ax1 may not overlap a center O1 of the first couch 100 or a center O2 of the second couch 200. In other words, the first axis Ax1 is disposed at a position different from the center O1 of the first couch 100 or the center O2 of the second couch 200 and, for example, may be disposed biased to a region in which the epigastrium of the patient is positioned. Since there are many cases where a radiation treatment target is positioned on the epigastrium of the patient, the adjustable couch 20 enables accurate adjustment of the yaw direction for a radiation treatment position through the rotation about the first axis Ax1 disposed to be biased as described above.

Referring to FIG. 3b, in another embodiment, a rotating-coupling means b2 is formed of a protrusion, and may include a pillar portion b21 protruding from a lower surface 200B of a second couch 200 and a fixing portion b22 provided on one side of the pillar portion b21. Here, a diameter of the fixing portion b22 may be greater than a diameter of the pillar portion b21. A second groove g2 of a first couch 100 is formed in a shape corresponding thereto and, particularly, may be formed of a guide groove g21 corresponding to the pillar portion b21 and a fixing groove g22 corresponding to the fixing portion b22. That is, as the fixing portion b22 of the rotating-coupling means b2 is engaged in the fixing groove g22 of the second groove g2, the second couch 200 may rotate about the first axis Ax1 while being fixed to the first couch 100. The technical idea of the present disclosure is not limited thereto, and it is possible for the rotating-coupling means b2 to have any form enabling the second couch 200 to be rotatably coupled to the first couch 100.

Meanwhile, the rotating-coupling means b2 is formed extending from the second couch 200 and may be constituted by the same material as the second couch 200. In an embodiment, the second couch 200 may be constituted by a carbon material through which the radiation may be transmitted, and the first couch 100 may also be constituted by the same carbon material. The radiation irradiation unit of the radiation treatment device 11 is disposed below the medical couch 12 and may irradiate a patient with the radiation, but when the adjustable couch 20 disposed above the medical couch 12 is constituted by a material preventing the transmission of radiation, it may be difficult to perform accurate treatment. In the adjustable couch 20 according to an embodiment of the present disclosure, as at least a region irradiated with the radiation is formed of only a material through which the radiation is transmitted, it is possible to perform more accurate radiation treatment. When the rotating-coupling means b2 is constituted by the pillar portion b21 and the fixing portion b22 as illustrated in FIG. 3b, it is reasonable that they are also constituted by a carbon material.

Referring to FIG. 2 again, the second couch 200 may be further provided with a rotation angle checking portion 210 through which a rotation angle about the first axis Ax1 may be checked. The adjustable couch 20 may be further provided with a rotation driving means for rotating the second couch 200 about the first axis Ax1, but the rotation driving means is not further provided, and a user may manually rotate the second couch 200. When the second couch 200 is rotated manually, a separate rotation driving means is not necessary, and thus the entire adjustable couch 20 may be constituted by a radiation transmittable material, enabling the accurate radiation treatment as described above. If the rotation driving means is provided, the rotation driving means is provided at a position spaced a certain distance from a radiation irradiated region, and thus the radiation in the radiation irradiated region may be transmitted as much as possible.

A user may check a rotation degree of the second couch 200 through the rotation angle checking portion 210. The rotation angle checking portion 210 may be provided as a through-hole passing through the second couch 200. Through the through-hole of the rotation angle checking portion 210, a reference line L1 provided in the upper surface 100A of the first couch 100 may be checked. The rotation angle checking portion 210 is further provided with an angle display portion 211 adjacent to the through-hole, and after the zero point is set with respect to the reference line L1, the angle due to rotation may be checked. Here, the reference line L1 may be formed along a second axis Ax2 that crosses the first axis Ax1 and passes the center O1 of the first couch 100. The reference line L1 may be formed over the entire region along the second axis Ax2 as illustrated in FIG. 2, but may be formed only in a region which may be checked in the rotation angle checking portion 210.

Figure 4:
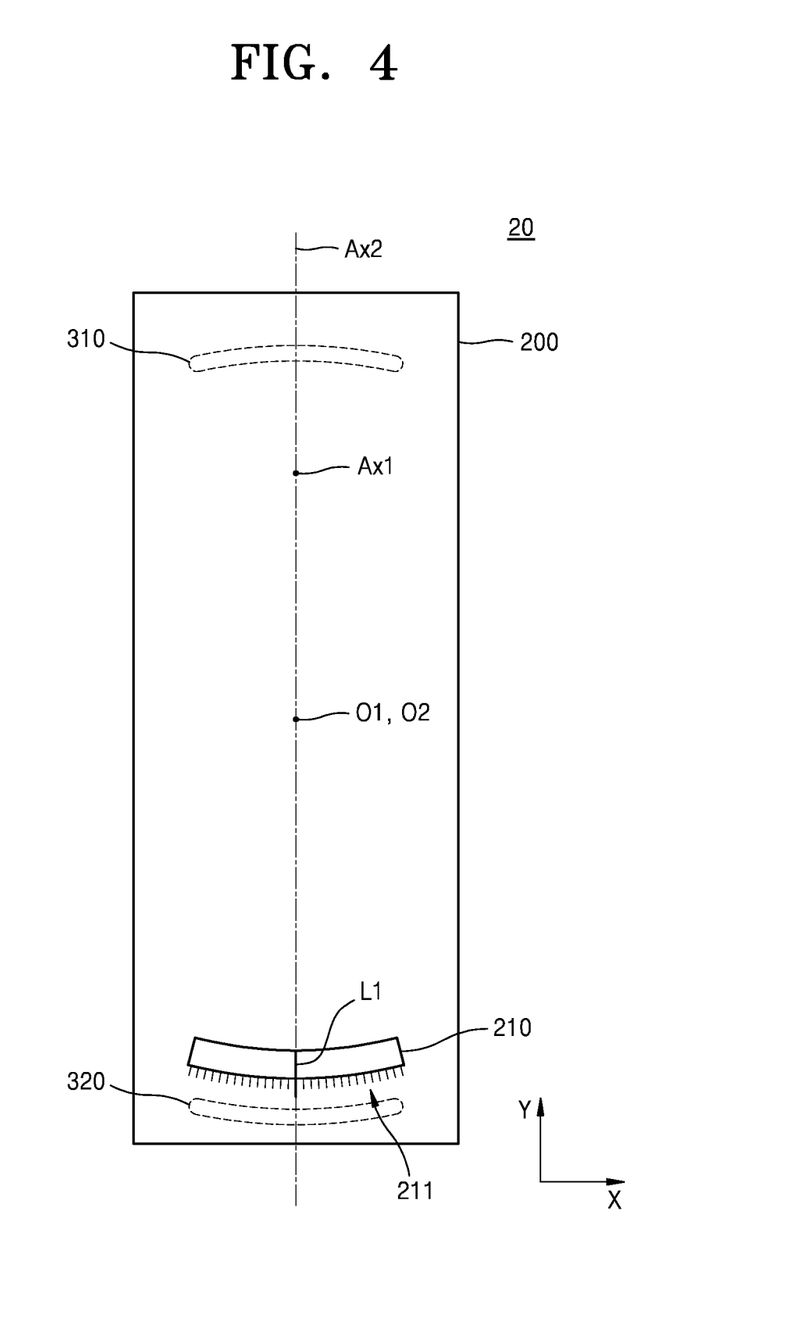
FIGS. 4 and 5 are views for describing that an adjustable couch according to an embodiment of the present disclosure is adjusted in a yaw direction.
Figure 5:
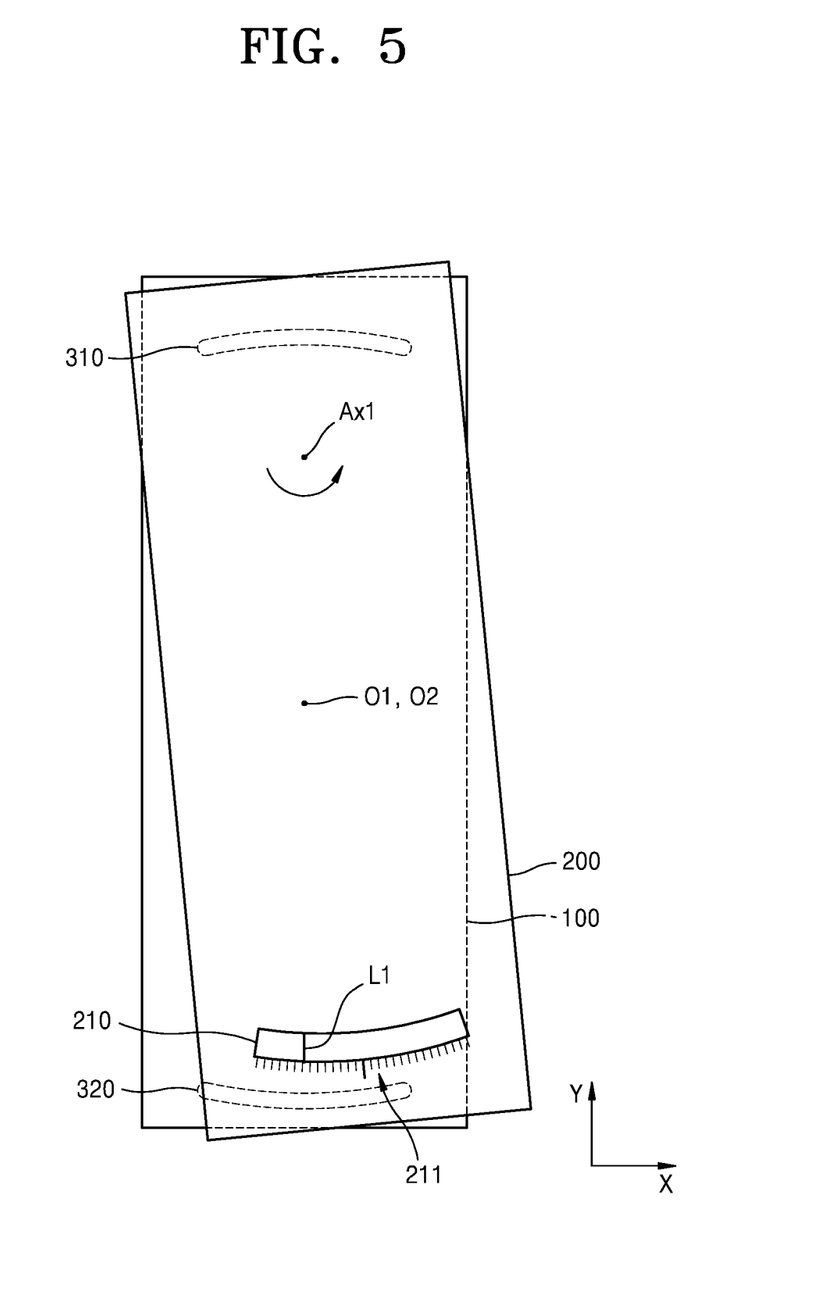

FIGS. 4 and 5 are views for describing that the adjustable couch 20 according to an embodiment of the present disclosure is adjusted in the yaw direction.

Referring to FIGS. 4 and 5, a user who is an inspector sets the zero point with respect to the reference line L1 formed in the first couch 100 in a state in which the adjustable couch 20 is mounted to the medical couch 12. Subsequently, the medical couch 12 enters the bore of the gantry to obtain a medical image, and here, the medical couch system 1 may compare the medical image with a treatment planning image obtained when a user works out a radiation treatment plan, and derive how much the medical couch 12 is tilted in the yaw direction. The inspector may be informed of the degree of tilting derived as above through a display portion (not shown) that displays a result value to the outside. Subsequently, the inspector rotates the second couch 200 by the above-described result value with respect to the first couch 100 and positions the patient on a correct position when the radiation treatment planning is worked out, and then the radiation treatment may be performed.

Here, the adjustable couch 20 may include at least one of a first guide rail 310 and a second guide rail 320 between the first couch 100 and the second couch 200, which guide the rotation of the second couch 200. The first guide rail 310 may be positioned in an upper portion of the adjustable couch 20, and the second guide rail 320 may be positioned in a lower portion of the adjustable couch 20. As the first guide rail 310 and the second guide rail 320 are disposed spaced apart from the radiation irradiated region, interference in the transmittance of radiation due to other components in the radiation irradiated region may be reduced as much as possible.

As described above, the adjustable couch according to embodiments of the present disclosure is provided detachably on the medical couch, and thus it is not necessary to replace the entire medical couch used in radiation treatment for adjustment in the yaw direction, thereby making it possible to achieve an effect of reducing costs. Also, the adjustable couch is adjusted in the yaw direction, and then the radiation treatment may be performed. Through this, the medical couch system may not only decrease the number of retakes as much as possible to reduce the total treatment time, but also accordingly reduce the risk of developing secondary cancer, increase the patient reproducibility, and reduce pains.

Therefore, the spirit of the present disclosure should not be limited and determined by the above-described embodiments, and not only the claims which will be described below but also all the scope equivalent to the claims or equivalently modified therefrom fall within the scope of the spirit of the present disclosure.

INDUSTRIAL APPLICABILITY

According to the present disclosure, provided is an adjustable couch that can be mounted on a medical couch. Also, embodiments of the present disclosure may be applied to a medical couch or the like used in industry.

The invention claimed is:

1. An adjustable couch detachable on a medical couch, the adjustable couch comprising:
   a first couch provided with a fixing means fixing the adjustable couch to the medical couch; and
   a second couch disposed on the first couch and provided with a rotating-coupling means to be coupled rotatably about a first axis perpendicular to an upper surface of the first couch, and
   wherein the rotating-coupling means comprise a second protrusion which is disposed on a lower surface of the second couch which is in contact with the upper surface of the first couch,
   wherein the first couch comprises a second groove which is formed on the upper surface of the first couch and corresponding to the second protrusion, and
   wherein the second groove and the second protrusion are each coaxial with the first axis, and the second protrusion is inserted into the second groove and rotates about the first axis.

2. The adjustable couch of claim 1, wherein the fixing means is disposed on a lower surface of the first couch on an opposite side from the upper surface, and is constituted by one or more first protrusions corresponding to one or more first grooves provided in the medical couch.

3. The adjustable couch of claim 2, wherein, when the first grooves are constituted by a plurality grooves, a number of the first protrusions is less than a number of the first grooves.

4. The adjustable couch of claim 1, wherein the rotating-coupling means is constituted by a same material as the second couch.

5. The adjustable couch of claim 1, wherein the rotating-coupling means is disposed on the first axis, but is disposed at a position different from a center of the first couch.

6. The adjustable couch of claim 1, wherein the second couch is further provided with a rotation angle checking portion through which a rotation angle about the first axis is checked.

7. A medical couch system comprising:
a medical couch provided with one or more first grooves;
a support for supporting the medical couch; and
an adjustable couch which is detachably mounted on the medical couch, and comprises a first couch provided with a fixing means fixing the adjustable couch to the medical couch and a second couch disposed on the first couch and provided with a rotating-coupling means to be coupled rotatably about a first axis perpendicular to an upper surface of the first couch, and
wherein the rotating coupling means comprise a second protrusion which is disposed on a lower surface of the second couch which is in contact with the upper surface of the first couch,
wherein the first couch comprises a second groove which is formed on the upper surface of the first couch and corresponding to the second protrusion, and
wherein the second groove and the second protrusion are each coaxial with the first axis, and the second protrusion is inserted into the second groove and rotates about the first axis.

8. The medical couch system of claim 7, wherein the fixing means is disposed on a lower surface of the first couch on an opposite side from the upper surface, and is constituted by one or more first protrusions corresponding to one or more first grooves provided in the medical couch.

9. The medical couch system of claim 8,
wherein the first grooves are constituted by a plurality of grooves and disposed at both edges on an upper surface of the medical couch along a first direction in which a length of the medical couch extends, and
wherein a number of the first protrusions is less than a number of the first grooves.

10. The medical couch system of claim 7, wherein the rotating-coupling means is constituted by a same material as the second couch.

11. The medical couch system of claim 7, wherein the rotating-coupling means is disposed on the first axis, but is disposed at a position different from a center of the first couch.

12. The medical couch system of claim 7, wherein the second couch is further provided with a rotation angle checking portion through which a rotation angle about the first axis is checked.

* * * * *